United States Patent

Sakurai et al.

[11] Patent Number: 5,998,668
[45] Date of Patent: Dec. 7, 1999

[54] OPTICALLY ACTIVE COMPOUND AND PROCESS FOR PRODUCING THE SAME

[75] Inventors: Kazutoshi Sakurai; Kenya Ishida; Miharu Ogura, all of Kanagawa, Japan

[73] Assignee: Takasago International Corporation, Tokyo, Japan

[21] Appl. No.: 09/017,239

[22] Filed: Feb. 2, 1998

[30] Foreign Application Priority Data

Jan. 31, 1997 [JP] Japan ............................... 9-031508

[51] Int. Cl.$^6$ .......................... C07C 233/05; C07C 231/02
[52] U.S. Cl. ............................ 564/203; 564/134; 564/141; 564/201
[58] Field of Search .................... 564/201, 203, 564/134, 141

[56] References Cited

U.S. PATENT DOCUMENTS 5,519,007  5/1996  Valle et al. .............................. 514/23

FOREIGN PATENT DOCUMENTS 0373038  6/1990  European Pat. Off. .
9715272  5/1997  WIPO .

Primary Examiner—Shailendra Kumar
Attorney, Agent, or Firm—Sughrue, Mion, Zinn, Macpeak & Seas, PLLC

[57] ABSTRACT

An optically active (2S,3R)-2-(3'-hydroxyacyl) aminoalkane-1,3-diol and a process for producing the same are disclosed. The compound is represented by the following general formula (1):

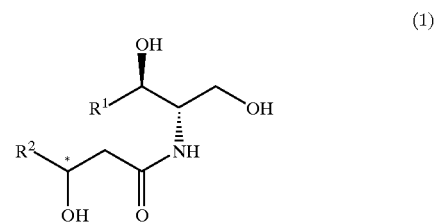

(1)

wherein $R^1$ represents a linear or branched, saturated aliphatic hydrocarbon group having 9 to 19 carbon atoms; $R^2$ represents a linear or branched, saturated aliphatic hydrocarbon group having 1 to 19 carbon atoms; and symbol * means that the carbon atom is an asymmetric carbon atom of the S or R configuration. The optically active compound is a ceramide in which the fatty acid moiety has an optically active hydroxyl group in the 3-position.

4 Claims, No Drawings

OPTICALLY ACTIVE COMPOUND AND PROCESS FOR PRODUCING THE SAME

FIELD OF THE INVENTION

The present invention relates to an optically active (2S,3R)-2-(3'-hydroxyacyl)aminoalkane-1,3-diol and a process for producing the same.

BACKGROUND OF THE INVENTION

Ceramides are specific sphingolipids which exist in intercellular lipid lamellae of horny layers. Ceramides are known to function, in skin epidermises, to retain moisture and as a barrier against water penetration. Various ceramides have been isolated from horny layers of skins of mammals such as human, horse, bovine, and swine and from brains and other organs of such mammals, and identified. It has been reported that various kinds of ceramides exist which are roughly classified under Types 1 to 6 (see D. T. Downing et al., *J. Invest. Dermatol.*, vol. 84, p. 410 (1985)).

The ceramides each is constituted of a sphingosine base moiety and a fatty acid moiety bonded thereto through an amide bond. Among these, the ceramides classified under Types 4 to 6 have a hydroxyl group in the fatty acid moiety in the position adjacent to the carbonyl group. Namely, this hydroxy acid having the hydroxyl group constitutes an α-hydroxy fatty acid (2-hydroxy fatty acid). It is also known that in each of these ceramides, the sphingosine base moiety is an optically active part of the (2S,3R) configuration, while the 2-hydroxy fatty acid moiety is an optically active part of the (R) configuration.

As described above, such 2-hydroxy fatty acid moieties having the hydroxyl group therein, including the optically active moieties described above, have been known. On the other hand, with respect to 3-hydroxy fatty acid moieties having the hydroxyl group therein, racemic 3-hydroxyvaleric acid is given in JP-A-2-200691 as an example of lower saturated acids from which N-acyl groups are to be formed. (The term "JP-A" as used herein means an "unexamined published Japanese patent application".) However, there is no description therein concerning a specific process for producing a ceramide using an optically active 3-hydroxy acid or concerning physicochemical data for such a ceramide.

SUMMARY OF THE INVENTION

An object of the present invention is to provide a novel optically active ceramide in which the fatty acid moiety has an optically active hydroxyl group in the 3-position. Another object of the present invention is to provide a process for producing the ceramide.

The present inventors synthesized various ceramides and investigated the properties thereof. In the course of the investigations, they directed attention to ceramides having a 3-hydroxy fatty acid within the molecule and made intensive studies thereon. As a result, they have found that when an optically active (2S,3R)-2-aminoalkane-1,3-diol is reacted with an optically active 3-hydroxyalkanoic acid ester in an alcohol solvent in the presence of a basic catalyst while the lower alcohol yielded during the reaction is kept being removed from the reaction system by distillation, then an N-acylation reaction proceeds selectively and an optically active ceramide having a 3-hydroxy fatty acid in the molecule can be produced. The present invention has been completed based on this finding.

The present invention provides a novel, optically active (2S,3R)-2-(3'-hydroxyacyl)aminoalkane-1,3-diol represented by the following general formula (1):

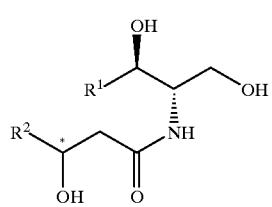

(1)

wherein $R^1$ represents a linear or branched, saturated aliphatic hydrocarbon group having 9 to 19 carbon atoms; $R^2$ represents a linear or branched, saturated aliphatic hydrocarbon group having 1 to 19 carbon atoms; and the symbol * means that the carbon atom is an asymmetric carbon atom of the S or R configuration.

The present invention furthermore provides a process for producing an optically active (2S,3R)-2-(3'-hydroxyacyl)aminoalkane-1,3-diol represented by the following general formula (1):

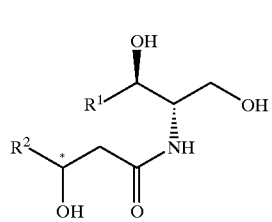

(1)

wherein $R^1$ represents a linear or branched, saturated aliphatic hydrocarbon group having 9 to 19 carbon atoms; $R^2$ represents a linear or branched, saturated aliphatic hydrocarbon group having 1 to 19 carbon atoms; and the symbol * means that the carbon atom is an asymmetric carbon atom of the S or R configuration, which comprises reacting an optically active (2S,3R)-2-aminoalkane-1,3-diol represented by the following general formula (2):

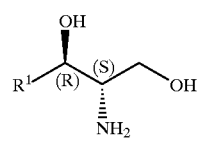

(2)

wherein $R^1$ is the same as defined in general formula (1), with an optically active 3-hydroxyalkanoic acid ester represented by the following general formula (3):

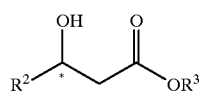

(3)

wherein $R^1$ is the same as defined in general formula (1); $R^3$ represents a lower alkyl group; and the symbol * is the same as defined in general formula (1), in an alcohol solvent in the presence of a basic catalyst, while the lower alcohol yielded during the reaction is kept from being removed from the reaction system by distillation.

DETAILED DESCRIPTION OF THE INVENTION

The optically active (2S,3R)-2-(3'-hydroxyacyl) aminoalkane-1,3-diol represented by general formula (1) of the present invention is a novel compound. Examples thereof include (2S,3R,3'R)-2-(3'-hydroxyacyl) aminoalkane-1,3-diols, in each of which the fatty acid moiety is of the (R) configuration in the 3'-position, and (2S,3R,3'S)-2-(3'-hydroxyacyl)aminoalkane-1,3-diols, in each of which the fatty acid moiety is of the (S) configuration in the 3'-position.

The optically active (2S,3R)-2-(3'-hydroxyacyl) aminoalkane-1,3-diol represented by general formula (1) can be produced by reacting an optically active (2S,3R)-2-amino-1,3-diol represented by general formula (2) with an optically active 3-hydroxyalkanoic acid ester represented by general formula (3) in an alcohol solvent in the presence of a basic catalyst while the lower alcohol yielded during the reaction is kept from being removed from the reaction system by distillation. That is, the compound of the present invention can be produced by conducting the selective N-acylation reaction of the diol.

According to this process, use of the (R) isomer of a 3-hydroxyalkanoic acid ester represented by general formula (3) gives a (2S,3R,3'R)-2-(3'-hydroxyacyl) aminoalkane-1,3-diol, while use of the (S) isomer of a 3-hydroxyalkanoic acid ester represented by general formula (3) gives a (2S,3R,3'S)-2-(3'-hydroxyacyl) aminoalkane-1,3-diol.

The optically active (2S,3R)-2-amino-1,3-diol represented by general formula (2), which is used as one of the reactants in the process of the present invention, can be synthesized, for example, according to the process described in JP-A-6-80617. This process is shown in Reaction Scheme 1 below.

Reaction Scheme 1

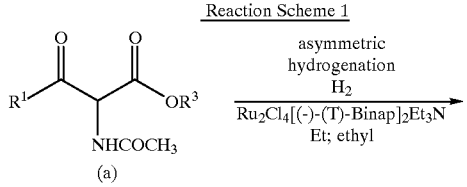

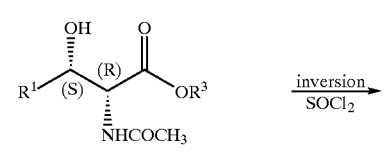

(b)

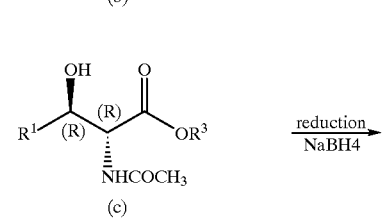

(c)

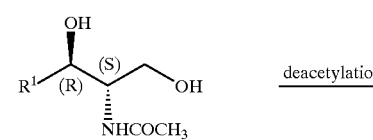

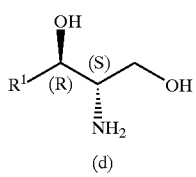

(d)

In this process, a 2-acetamino-3-oxoalkanoic acid ester (a) as a starting material is asymmetrically hydrogenated using a ruthenium-optically active phosphine complex as a catalyst to obtain an optically active (2R,3S)-2-acetamino-3-hydroxyalkanoic acid ester (b). The configuration of this optically active ester at the 3-position hydroxyl group is then inverted to obtain the (2R,3R) isomer (c), which is then subjected to reduction and deacetylation, whereby an optically active (2S,3R)-2-aminoalkane-1,3-diol (d) can be obtained.

In Reaction Scheme 1, $R^1$ and $R^2$ have the same meanings as defined in general formula (2) or (3), and (T)-BINAP means 2,2'-bis(di-p-tolylphosphino)-1,1'-binaphthyl.

The optically active 3-hydroxyalkanoic acid ester represented by general formula (3), as the other starting material for use in the reaction, can be synthesized, for example, according to the process described in JP-A-63-310847. This process is shown in Reaction Scheme 2 below.

Reaction Scheme 2

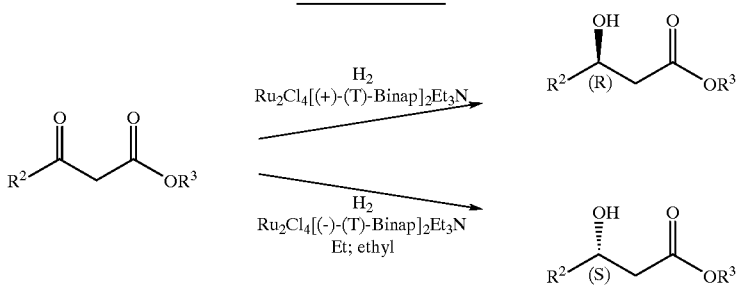

In this process, 3-oxoalkanoic acid ester (e) is asymmetrically hydrogenated using a ruthenium-optically active phosphine complex as a catalyst. Thus, the target ester having a high optical purity can be obtained through one step. In this reaction also, optically active esters represented by general formula (3) which differ in configuration can be obtained by using catalysts which differ in the absolute configuration of the ligand. Namely, use of the (+) isomer of an optically active phosphine complex gives an (R)-3-hydroxyalkanoic acid ester, while use of the (−) isomer of the optically active phosphine complex gives an (S)-3-hydroxyalkanoic acid ester.

Examples of the thus-obtained 3-hydroxyalkanoic acid ester include compounds represented by general formula (3) wherein $R^2$ is a linear or branched, saturated aliphatic hydrocarbon group having 1 to 19 carbon atoms and $R^3$ is a lower alkyl group having 1 to 4, preferably 1 or 2 carbon atoms. Specific examples thereof are as follows.

Specific examples of these compounds represented by general formula (3) include methyl and ethyl esters of saturated fatty acids which esters each is of the (R) or (S) configuration, such as methyl 3-hydroxybutanoate, ethyl 3-hydroxybutanoate, methyl 3-hydroxypentanoate, ethyl 3-hydroxypentanoate, methyl 3-hydroxyhexanoate, ethyl 3-hydroxyhexanoate, methyl 3-hydroxyheptanoate, ethyl 3-hydroxyheptanoate, methyl 3-hydroxyoctanoate, ethyl 3-hydroxyoctanoate, methyl 3-hydroxynonanoate, ethyl 3-hydroxynonanoate, methyl 3-hydroxydecanoate, ethyl 3-hydroxydecanoate, methyl 3-hydroxyundecanoate, ethyl 3-hydroxyundecanoate, methyl 3-hydroxydodecanoate, ethyl 3-hydroxydodecanoate, methyl 3-hydroxytridecanoate, ethyl 3-hydroxytridecanoate, methyl 3-hydroxytetradecanoate, ethyl 3-hydroxytetradecanoate, methyl 3-hydroxypentadecanoate, ethyl 3-hydroxypentadecanoate, methyl 3-hydroxyhexadecanoate, ethyl 3-hydroxyhexadecanoate, methyl 3-hydroxy-15-methylhexadecanoate, ethyl 3-hydroxy-15-methylhexadecanoate, methyl 3-hydroxyheptadecanoate, ethyl 3-hydroxyheptadecanoate, methyl 3-hydroxyoctadecanoate, ethyl 3-hydroxyoctadecanoate, methyl 3-hydroxynonadecanoate, ethyl 3-hydroxynonadecanoate, methyl 3-hydroxyeicosanoate, ethyl 3-hydroxyeicosanoate, methyl 3-hydroxydocosanoate, ethyl 3-hydroxydocosanoate, methyl 3-hydroxyheneicosanoate, and ethyl 3-hydroxyheneicosanoate. However, the optically active compound represented by general formula (3) is not limited to these examples.

In the process of the present invention, the optically active 3-hydroxyalkanoic acid ester represented by general formula (3) is used in an amount of from 1.0 to 1.5 mols, preferably from 1.0 to 1.2 mols, per mol of the (2S,3R)-2-amino-1,3-diol represented by general formula (2).

Examples of the alcohol solvent used in the reaction include alcohols having 2 to 8 carbon atoms. Specific examples thereof include ethanol, propyl alcohol, isopropyl alcohol, n-butyl alcohol, isobutyl alcohol, t-butyl alcohol, amyl alcohol, hexyl alcohol, heptyl alcohol, and octyl alcohol. These alcohols can be used alone or as a mixture of two or more thereof.

The target compound produced by the process of the present invention is relatively easily dispersible in alcohols. In particular, in the case where n-butyl alcohol was used to carry out the process, the target compound can be crystallized out by merely cooling the resultant n-butyl alcohol solution after completion of the reaction, without using any other solvent. This target compound can be purified by recrystallization from methanol or ethanol.

In conducting the reaction, if the amount of the alcohol solvent used is too small, the (2S,3R)-2-aminoalkane-1,3-diol represented by general formula (2) undergoes esterification at the alcoholic hydroxyl group bonded to a primary carbon atom, thereby giving an ester which has good crystallizability and is hence difficult to remove from the reaction mixture solution by recrystallization or other techniques. Consequently, the alcohol solvent is used in this reaction in an amount of from 1 to 10 times (volume/weight), preferably from 3 to 8 times (volume), the amount of the (2S,3R)-2-aminoalkane-1,3-diol represented by general formula (2).

Examples of the basic catalyst for use in the process of the present invention include sodium hydroxide, potassium hydroxide, potassium carbonate, sodium methoxide, and sodium ethoxide. These basic catalysts can be used usually in an amount of from 0.01 to 0.2 mol per mol of the optically active 3-hydroxyalkanoic acid ester represented by general formula (3).

In the reaction in the present invention, the amino group of the (2S,3R)-2-aminoalkane-1,3-diol represented by general formula (2) is selectively converted to an N-acyl group. During this reaction, the lower alcohol which generates as a result of the acylation reaction, e.g., methanol or ethanol, is kept from being removed from the reaction system by distillation either at a reduced pressure or while introducing a gas such as, e.g., nitrogen or air. Thus, the reaction can be efficiently carried out. In the case where the reaction is conducted at a reduced pressure, the reaction can be conducted usually at from 30 to 100 mmHg and from 50 to 120° C. In the case where nitrogen gas, among gases including air and nitrogen, is introduced, the reaction is conducted with heating at 90 to 120° C. while introducing $N_2$ at a flow rate of about 100 ml/min.

In conducting the reaction, a 3-hydroxyalkanoic acid ester represented by general formula (3) can be added to a mixture of a (2S,3R)-2-aminoalkane-1,3-diol represented by general formula (2), sodium or potassium hydroxide, and n-butyl alcohol. The ester represented by general formula (3) may be added dropwise over a period of about 15 minutes, or added at a time to the mixture which has been heated to 90 to 95° C. The reaction time is usually from 0.5 to 6 hours, preferably from 1 to 2 hours.

After completion of the reaction, the reaction mixture solution is taken out of the reactor and cooled to a temperature of from room temperature to −30° C., whereby an optically active (2S,3R)-2-(3'-hydroxyacyl)aminoalkane-1,3-diol represented by general formula (1) as the target compound is precipitated as crude crystals. These crude crystals are taken out by filtration and recrystallized from methanol, ethanol, acetonitrile, or the like. Thus, impurities can be easily removed to purify the target compound.

The novel, optically active (2S,3R)-2-(3'-hydroxyacyl)aminoalkane-1,3-diol represented by general formula (1), which is obtained according to the present invention and has a 3-hydroxy fatty acid in the molecule, functions not only to highly effectively retain moisture but also as a barrier on skin epidermises. Therefore, the compound is expected to be useful as a base for cosmetics.

According to the process of the present invention, the target compound can be produced in high yield without causing crystal precipitation during the reaction, and without the necessity of conducting a troublesome operation, e.g., extraction, in a purification step after completion of the reaction. Therefore, the process is advantageous industrially and economically.

Further, of the optically active (2S,3R)-2-(3'-hydroxyacyl)aminoalkane-1,3-diols represented by general formula (1), that compound wherein the hydroxy group at the 3'-position is (R)-isomer, $R^1$ is 11-methyldodecyl group, $R^2$ is 13-methyltetradecyl group, and the hydroxy group at the 1-position is converted into sulfonic acid group, is called "Sulfobacin A", which has a prophylactic effect of thrombus in cerebrum or organism as von Willebrand factor receptor, as reported in *J. Antibiotics.*, Vol. 48, p. 924 (1995) and *J. Antibiotics.*, Vol. 48, p. 929 (1995). Furthermore, the same compound is also called "Flavocristamide B", which is showed as polymerase α inhibitor, as reported in *Tetrahedron*, Vol. 51, p. 10478 (1995). Therefore, the optically active (2S,3R)-2-(3'-hydroxyacyl)aminoalkane-1,3-diol of the present invention is a very important compound as a medicinal intermediate.

The present invention will be explained below in more detail by reference to Reference Examples and Examples, but the invention should not be construed as being limited to these Examples. For analyses in the Examples, the following apparatuses and conditions were used unless otherwise indicated.

(Apparatuses and Conditions for Analyses)
High-Performance Liquid Chromatography
  Apparatus: L6200 (manufactured by Hitachi, Ltd., Japan) Detector: UV detector L4000 (manufactured by Hitachi, Ltd.)
Nuclear Magnetic Resonance Spectrometry
  Apparatus: Type AM-400, 400 MHz (manufactured by Bruker, Inc.)
  Internal reference: tetramethylsilane
Specific Rotation
  Apparatus: Type DIP-4 (manufactured by JASCO Corporation, Japan)
Elemental Analysis
  Apparatus: CHN-2400 (manufactured by Perkin Elmer Corp.)
Mass Spectrometry
  Apparatus: M80B (manufactured by Hitachi, Ltd.)
Melting Point Measurement
  Apparatus: MP-S3 (manufactured by Yanagimoto Shoji K.K., Japan)

REFERENCE EXAMPLE 1

Synthesis of methyl (R)-3-hydroxyoctadecanoate
(1) Methyl 3-Oxooctadecanoate

Four liters of a suspension of 440 g (11 mol) of 60% sodium hydride in dried tetrahydrofuran was cooled to 0° C. Thereto was added dropwise 1.8 L of a tetrahydrofuran solution of 1.161 kg (10 mol) of methyl acetoacetate. After this mixture was stirred at room temperature for 1 hour, 3.023 kg (11 mol) of hexadecanoyl chloride was added dropwise at 0 to 5° C. and the resultant mixture was stirred at room temperature overnight. Thereafter, the tetrahydrofuran was distilled off, and the residue was poured into ice water and extracted with 8 L of ethyl acetate. The ethyl acetate was distilled off, and the residue was poured into a mixture of 400 g of a 28% methanol solution of sodium methoxide and 1.2 L of methanol. The resultant mixture was stirred with heating at 60 to 65° C. for 6 hours. The reaction mixture was cooled with ice, and the pH thereof was then adjusted to 5 with 10% sulfuric acid. This reaction mixture was extracted with ethyl acetate. The ethyl acetate layer was washed with 5% aqueous sodium carbonate solution and saturated aqueous common salt solution. Thereafter, the ethyl acetate was distilled off and the concentrate was recrystallized from methanol to obtain 1.72 kg (5.5 mol) of methyl 3-oxooctadecanoate. Yield, 55%.

Melting point: 45° C.

(2) Methyl (R)-3-Hydroxyoctadecanoate

Into a 200-ml autoclave (made of Hastelloy) were introduced 50 g of the methyl 3-oxooctadecanoate obtained above and 50 ml of methanol. The atmosphere in the autoclave was replaced with nitrogen gas. Thereto was added a solution prepared by dissolving 325 mg of $Ru_2Cl_4$ ((+)-(T)BINAP)$_2$Et$_3$N as a ruthenium-optically active phosphine complex in 3.8 ml of methylene chloride. Asymmetric hydrogenation was conducted at 65° C. and a hydrogen pressure of 30 atm. After the reaction mixture was thus reacted for 12 hours, it was taken out of the autoclave. The reaction product was recrystallized from methanol to obtain 47.8 g of methyl (R)-3-hydroxyoctadecanoate. Yield, 95%.

Melting point: 38–40° C.; Specific rotation $[\alpha]_D^{25}$: −4.50 (c=1.0, $CHCl_3$)

The optical purity of this compound was determined by reacting the compound with (R)-(+)-α-methoxy-α-trifluoromethylphenylacetic acid (hereinafter referred to as "MTPA") in methylene chloride in the presence of N,N'-dicyclohexylcarbodiimide and a catalytic amount of 4-dimethylaminopyridine to synthesize an MTPA ester and then analyzing the ester by high-performance liquid chromatography. As a result, the optical purity thereof was found to be 98% e.e.

REFERENCE EXAMPLE 2

Synthesis of methyl (R)-3-hydroxypentanoate

Into a 200-ml autoclave (made of Hastelloy) were introduced 50 g of methyl 3-oxopentanoate (manufactured by Wacker Chemicals Co., Ltd.) and 75 ml of methanol. The atmosphere in the autoclave was replaced with nitrogen gas. Thereto was added a solution prepared by dissolving 325 mg of Ru$_2$Cl$_4$((+)-(T)BINAP)$_2$Et$_3$N as a ruthenium-optically active phosphine complex in 3.8 ml of methylene chloride. Asymmetric hydrogenation was conducted at a reaction temperature of 30° C. and a hydrogen pressure of 30 atm. After the reaction mixture was thus reacted for 50 hours, it was taken out of the autoclave. The methanol was distilled off, and the residue was subjected to vacuum distillation to obtain 49.8 g of methyl (R)-3-hydroxypentanoate. Yield, 98%.

Boiling point: 66° C. /2 mmHg; Specific rotation $[\alpha]_D^{25}$: −46.50 (c=1.0, CHCl$_3$)

The optical purity of this compound was determined by high-performance liquid chromatography. As a result, it was found to be 99.3% e.e.

REFERENCE EXAMPLE 3
Synthesis of methyl (R)-3-hydroxyoctanoate

Into a 100-ml autoclave (made of Hastelloy) were introduced 20 g of methyl 3-oxooctanoate (manufactured by Inoue Perfumery Mfg. Co., Ltd., Japan) and 40 ml of methanol. The atmosphere in the autoclave was replaced with nitrogen gas. Thereto was added a solution prepared by dissolving 150 mg of Ru$_2$Cl$_4$((+)-(T)BINAP)$_2$Et$_3$N as a ruthenium-optically active phosphine complex in 1.2 ml of methylene chloride. Asymmetric hydrogenation was conducted at a reaction temperature of 65° C. and a hydrogen pressure of 30 atm. After the reaction mixture was thus reacted for 6 hours, it was taken out of the autoclave. The methanol was distilled off, and the residue was subjected to vacuum distillation to obtain 19.2 g of methyl (R)-3-hydroxyoctanoate. Yield, 95%.

Boiling point: 85° C./0.1 mmHg Specific rotation $[\alpha]_D^{25}$: −4.50 (c=1.0, CHCl$_3$)

The optical purity of this compound was determined by high-performance liquid chromatography. As a result, it was found to be 98.5% e.e.

REFERENCE EXAMPLE 4
Synthesis of methyl (S)-3-hydroxvoctanoate

Into a 100-ml autoclave (made of Hastelloy) were introduced 20 g of methyl 3-oxooctanoate (manufactured by Inoue Perfumery Mfg. Co., Ltd.) and 50 ml of methanol. The atmosphere in the autoclave was replaced with nitrogen gas. Thereto was added a solution prepared by dissolving 140 mg of Ru$_2$Cl$_4$((−)-(T)BINAP)$_2$Et$_3$N as a ruthenium-optically active phosphine complex in 1.0 ml of methylene chloride. Asymmetric hydrogenation was conducted at a reaction temperature of 65° C. and a hydrogen pressure of 30 atm. After the reaction mixture was thus reacted for 6 hours, it was taken out of the autoclave. The methanol was distilled off, and the residue was subjected to vacuum distillation to obtain 19.4 g of methyl (S)-3-hydroxyoctanoate. Yield, 96%.

Boiling point: 85° C. /0.1 mmHg; Specific rotation $[\alpha]_D^{25}$: +4.50 (c=1.0, CHCl$_3$)

The optical purity of this compound was determined by high-performance liquid chromatography. As a result, it was found to be 98.5% e.e.

EXAMPLE 1
Synthesis of (2S,3R,3'R)-2-(3'-hydroxyoctadecanoyl) aminooctadecane-1,3-diol Into a 300-ml four-necked flask equipped with a stirrer, dropping funnel, condenser, and bubble counter were introduced 0.66 g (0.01 mol) of 85% potassium hydroxide, 30.1 g (0.1 mol) of (2S,3R)-2-aminooctadecane-1,3-diol, and 150 ml of butanol. To the resultant suspension was added dropwise 31.4 g (0.10 mol) of methyl (R)-3-hydroxyoctadecanoate at 90° C. This mixture was reacted for 2 hours while introducing nitrogen gas (100 ml/min), and then cooled to −20° C. The crude crystals obtained were taken out by filtration and recrystallized from methanol to obtain 46.7 g of (2S,3R,3'R)-2-(3'-hydroxyoctadecanoyl) aminooctadecane-1,3-diol. Yield, 80.1%.

Melting point: 119.5–127° C.; Specific rotation $[\alpha]_D^{25}$: +3.97 (c=0.13, CHCl$_3$:MeOH=10:1); $^1$H-NMR (CDCl$_3$, δ ppm); 0.81 (t, 6H, J=7.0 Hz), 1.19 (brs, 50H), 1.33–1.61 (m, 10H), 2.20–2.53 (m,2H), 3.22–3.50 (m, 2H), 3.72 (m, 1H), 3.79 (m, 1H), 6.53 (d, 1H, J=7.8 Hz); MS: 584 (M$^+$+1); Elemental analysis; Calculated for C$_{36}$H$_{73}$NO$_4$ (%): C, 74.04; H, 12.60; N, 2.40; Found (%): C, 73.98; H, 12.45; N, 2.35

EXAMPLE 2
Synthesis of (2S,3R,3'S)-2-(3'-hydroxyoctadecanovl) aminooctadecane-1,3-diol The same procedure as in Example 1 was conducted, except that 30.1 g (0.1 mol) of (2S,3R)-2-aminooctadecane-1,3-diol and 31.4 g (0.1 mol) of methyl (S)-3-hydroxyoctadecanoate were used as reactants. Thus, 48.0 g of (2S,3R,3'S)-2-(3'-hydroxyoctadecanoyl) aminooctadecane-1,3-diol was obtained. Yield, 82.4%.

Melting point: 141–144° C.; Specific rotation $[\alpha]_D^{25}$: +2.99 (c=0.10, pyridine); $^1$H-NMR (pyridine-d$_5$, δ ppm); 0.87 (t, 6H, J=7.0 Hz), 1.27 (brs, 50H), 1.50–2.01 (m, 6H), 2.80 (m, 2H), 4.31 (m, 2H), 4.48 (m, 2H), 4.68 (m, 1H), 6.35 (m, 3H), 8.67 (d, 1H, J=8.6 Hz); MS: 584 (M$^+$+1); Elemental analysis; Calculated for C$_{36}$H$_{73}$NO$_4$ (%): C, 74.04; H, 12.60; N, 2.40; Found (%): C, 73.98; H, 12.45; N, 2.35

EXAMPLE 3
Synthesis of (2S,3R,3'R)-2-(3'-hydroxyoctanoyl) aminooctadecane-1,3-diol The same procedure as in Example 1 was conducted, except that 30.1 g (0.1 mol) of (2S,3R)-2-aminooctadecane-1,3-diol and 17.4 g (0.1 mol) of methyl (R)-3-hydroxyoctanoate were used as reactants. Thus, 39.2 g of (2S,3R,3'R)-2-(3'-hydroxyoctanoyl)aminooctadecane-1,3-diol was obtained. Yield, 88.2%.

Melting point: 127–134° C.; Specific rotation $[\alpha]_D^{25}$: +5.99 (c=0.10, CHCl$_3$:MeOH=10:1); $^1$H-NMR (pyridine-d$_5$, δ ppm); 0.88 (t, t, 6H, J=7.2, 6.8 Hz), 1.27 (brs, 28H), 1.40 (m, 1H), 1.58–1.80 (m, 4H), 1.80–2.02 (m, 3H), 2.75 (m, 2H), 4.30 (m, 2H), 4.47 (m, 2H), 4.70 (m, 1H), 6.35 (m, 3H), 8.67 (d, 1H, J=8.6 Hz); MS: 444 (M$^+$+1); Elemental analysis; Calculated for C$_{26}$H$_{53}$NO$_4$ (%): C, 70.38; H, 12.04; N, 3.16; Found (%): C, 70.30; H, 12.10; N, 3.07

EXAMPLE 4
Synthesis of (2S,3R,3'S)-2-(3'-hydroxyoctanoyl) aminooctadecane-1,3-diol The same procedure as in Example 1 was conducted, except that 30.1 g (0.1 mol) of (2S,3R)-2-aminooctadecane-1,3-diol and 17.4 g (0.1 mol) of methyl (S)-3-hydroxyoctanoate were used as reactants. Thus, 40.0 g of (2S,3R,3'S)-2-(3'-hydroxyoctanoyl)aminooctadecane-1,3-diol was obtained. Yield, 90.0%.

Melting point: 130–134° C.; Specific rotation $[\alpha]_D^{25}$: +18.01 (c=0.10, CHCl$_3$:MeOH=10:1); $^1$H-NMR (pyridine-d$_5$, δ ppm); 0.80 (t, 3H, J=7.1 Hz), 0.87 (t, 3H, J=6.8 Hz), 1.27 (brs, 28H), 1.40 (m, 1H), 1.58–1.80 (m, 4H), 1.80–2.02 (m, 3H), 2.75 (m, 2H), 4.27 (m, 1H), 4.47 (m, 2H), 4.69 (m, 1H), 6.28 (m, 1H), 6.37 (m, 2H), 8.67 (d, 1H, J=8.6 Hz); MS: 444 (M$^+$+1); Elemental analysis; Calculated for C$_{26}$H$_{53}$NO$_4$ (%): C, 70.38; H, 12.04; N, 3.16; Found (%): C, 70.25; H, 12.00; N, 3.12

EXAMPLE 5

Synthesis of (2S,3R,3'R)-2-(3'-hydroxypentanoyl)aminooctadecane-1,3-diol

The same procedure as in Example 1 was conducted, except that 30.1 g (0.1 mol) of (2S,3R)-2-aminooctadecane-1,3-diol and 13.2 g (0.1 mol) of methyl (R)-3-hydroxypentanoate were used as reactants. Thus, 33.1 g of (2S,3R,3'R)-2-(3'-hydroxypentanoyl)aminooctadecane-1,3-diol was obtained. Yield, 82.4%.

Melting point: 120–134° C.; Specific rotation $[\alpha]_D^{25}$: −14.98 (c=0.122, CHCl$_3$); $^1$H-NMR (pyridine-d$_5$, δ ppm); 0.88 (t, 3H, J=7.0 Hz), 1.04 (t, 3H, J=7.5 Hz), 1.27 (brs, 24H), 1.58 (m, 1H), 1.71 (m, 2H), 1.90 (m, 3H), 2.75 (m, 2H), 4.22–4.55 (m, 4H), 4.68 (m, 1H), 6.35 (m, 3H), 8.65 (d, 1H, J=8.7 Hz); MS: 402 (M$^+$+1); Elemental analysis; Calculated for C$_{23}$H$_{47}$NO$_4$ (%): C, 68.78; H, 11.79; N, 3.49; Found (%): C, 68.58; H, 11.86; N, 3.47

While the invention has been described in detail and with reference to specific embodiments thereof, it will be apparent to one skilled in the art that various changes and modifications can be made therein without departing from the spirit and scope thereof.

What is claimed is:

1. An optically active (2S,3R)-2-(3'-hydroxyacyl)aminoalkane-1,3-diol represented by the following general formula (1):

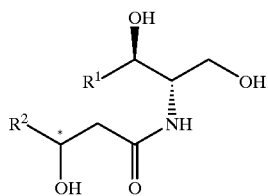

(1)

wherein R$^1$ represents a linear or branched, saturated aliphatic hydrocarbon group having 9 to 19 carbon atoms; R$^2$ represents a linear or branched, saturated aliphatic hydrocarbon group having 1 to 19 carbon atoms; and the symbol * means that the carbon atom is an asymmetric carbon atom of the S or R configuration.

2. A process for producing an optically active (2S,3R)-2-(3'-hydroxyacyl)aminoalkane-1,3-diol represented by the following general formula (1):

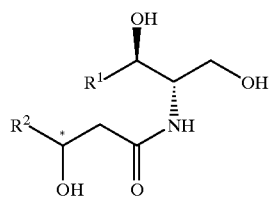

(1)

wherein R$^1$ represents a linear or branched, saturated aliphatic hydrocarbon group having 9 to 19 carbon atoms; R$^2$ represents a linear or branched, saturated aliphatic hydrocarbon group having 1 to 19 carbon atoms; and symbol * means that the carbon atom is an asymmetric carbon atom of the S or R configuration, which comprises reacting an optically active (2S,3R)-2-aminoalkane-1,3-diol represented by the following general formula (2):

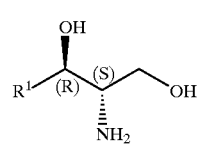

(2)

wherein R$^1$ is the same as defined in general formula (1), with an optically active 3-hydroxyalkanoic acid ester represented by the following general formula (3):

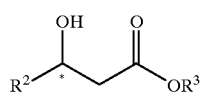

(3)

wherein R$^2$ is the same as defined in general formula (1); R$^3$ represents a lower alkyl group; and the symbol * is the same as defined in general formula (1), in an alcohol solvent in the presence of a basic catalyst, while lower alcohol yielded during the reaction is kept from being removed from the reaction system by distillation.

3. The process for producing an optically active (2S,3R)-2-(3'-hydroxyacyl)aminoalkane-1,3-diol of claim 2, wherein the alcohol solvent comprises an alcohol having 2 to 8 carbon atoms.

4. The process for producing an optically active (2S,3R)-2-(3'-hydroxyacyl)aminoalkane-1,3-diol of claim 2, wherein the alcohol solvent comprises n-butanol.

* * * * *